United States Patent
Hsieh

(10) Patent No.: US 6,215,841 B1
(45) Date of Patent: Apr. 10, 2001

(54) METHODS AND APPARATUS FOR 3D ARTIFACT REDUCTION

(75) Inventor: Jiang Hsieh, Brookfield, WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/162,283

(22) Filed: Sep. 29, 1998

(51) Int. Cl.[7] .................................................. A61B 6/03
(52) U.S. Cl. ............................ 378/8; 378/15; 378/901
(58) Field of Search ............................ 378/4, 8, 15, 99

(56) References Cited

U.S. PATENT DOCUMENTS 4,712,178 * 12/1987 Tuy et al. ................................. 378/9

OTHER PUBLICATIONS

Carl Crawford and Kevin King, "Computed Tomography Scanning with Simultaneous Patient Translation," Med. Phys. 17 (6), Nov./Dec. 1990, pp. 967–982.

Jiang Hsieh, "A general approach to the reconstruction of x–ray helical computed tomography," Med. Phys. 23 (2), Feb. 1996, pp. 221–229.

* cited by examiner

Primary Examiner—David V. Bruce
(74) Attorney, Agent, or Firm—Armstrong Teasdale LLP; Christian G. Cabou

(57) ABSTRACT

The present invention, in one form, is a system for reducing artifacts in three-dimensional image formation. More specifically, a 3D image generation algorithm is utilized to generate a composite boundary profile of the object. In one embodiment, the composite boundary profile is determined by selecting an appropriate threshold intensity level. In another embodiment, the composite boundary profile is determined by determining the slope of the boundary, the starting angle of the data set, and the algorithm for helical computed tomography reconstruction. The composite boundary profile is then adaptively filtered to remove inconsistency and thus remove image artifacts in the 3D images.

28 Claims, 4 Drawing Sheets

METHODS AND APPARATUS FOR 3D ARTIFACT REDUCTION

BACKGROUND OF THE INVENTION

This invention relates generally to computed tomography (CT) imaging and more particularly, to three dimensional artifact reduction in a CT system.

In at least one known CT imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighing algorithms which weight the collected data as a function of view angle and detector channel index. Specifically, prior to filtered back projection, the data is weighted according to a helical weighing factor, which is a function of both the gantry angle and detector angle. The helical weighting algorithms also scale the data according to a scaling factor, which is a function of the distance between the x-ray source and the object. The weighted and scaled data is then processed to generate CT numbers and to construct an image that corresponds to a two dimensional slice taken through the object.

It often is desirable to generate three-dimensional (3D) images or multi-planar reformatted images (herein referred to as 3-D images) of the object. Known algorithms for generating such images further process the helically weighted and scaled data. However, the 3D images typically include noticeable artifacts. Particularly, as a result of a heterogenous object being constantly translated during data acquisition, the attenuation distribution inside the scan plane changes continuously. To correct for this deviation from the basic tomographic reconstruction assumption, helical reconstruction is utilized to suppress the image artifacts. Recent developments of various computer graphic techniques applied to helical computed tomography, however, have discovered additional artifacts. These artifacts appear as periodical rings or grooves superimposed on the surface of the 3D image.

It would be desirable to provide an algorithm which facilitates the reduction of artifacts in 3D images due to the heterogenous object. It also would be desirable to provide such an algorithm which does not significantly increase the processing time.

BRIEF SUMMARY OF THE INVENTION

These and other objects may be attained in a system which, in one embodiment, includes a 3D image generation algorithm that reduces artifacts by determining object boundaries using an optimal intensity threshold. More particularly, and in accordance with one embodiment of the present invention, a threshold intensity level is selected, based on the intensity of the object as well as its background such that the 3D image artifact is minimized, to determine the composite boundary profile. This composite boundary profile, is then used to generate a 3D image of the object.

In accordance with another embodiment, the composite boundary profile is determined by determining the slope of the object boundary and a system edge response. This information, together with the weighting utilized in a helical reconstruction algorithm are used to determine a boundary error. Based on the boundary error information, adaptive filtering is then employed to reduce the inconsistency of the object boundary due to the helical reconstruction algorithm. More specifically, the object boundary profile for an axial scan is:

$$g(x) = \Gamma_{\frac{h}{k}} \otimes f$$

where:

$$\Gamma_{\frac{h}{k}}(x) = \begin{cases} 0 & x \leq 0 \\ \frac{kx}{h} & 0 < x < \frac{h}{k} \\ 1 & \text{Other} \end{cases}$$

f is a edge response of an imaging system;
k is a slope of the object boundary in x-z plane;
h is a slice thickness;
x is an image index variable; and
$\otimes$ represents a convolution.

For a helical scan, the composite boundary profile is:

$$g(x) = w_1 g_1(x-x_1) + w_2 g_2(x-x_2)$$

where:
$g_1$, $g_2$ are object boundary profiles (if axial scan were taken), as shown above;
$w_1$, $w_2$ are helical reconstruction weights associated with views that are perpendicular to the boundary which form a complimentary sampling pair;
$x_1$, $x_2$ are object boundary locations at two views that are perpendicular to the object boundary.

By generating the composite boundary profile as described above, the reduction of artifacts in 3D helical image reconstruction may be achieved by either adaptive filtering of the composite boundary or by adjusting the boundary location during 3D image generation. Particularly, by generating the 3D image using the above described process, reduces, and possibly eliminates, artifacts. Such algorithm also does not significantly increase the processing time.

DETAILED DESCRIPTION OF THE INVENTION

Figure 1:
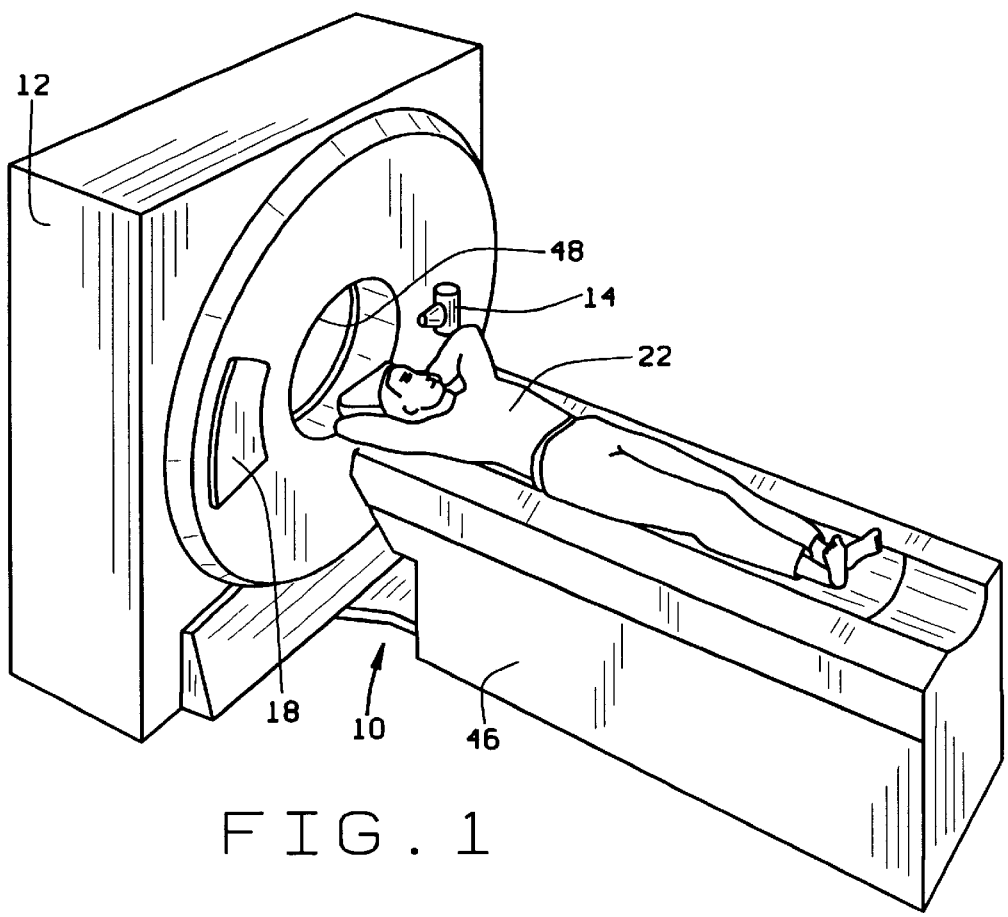
FIG. 1 is a pictorial view of a CT imaging system.
Figure 2:
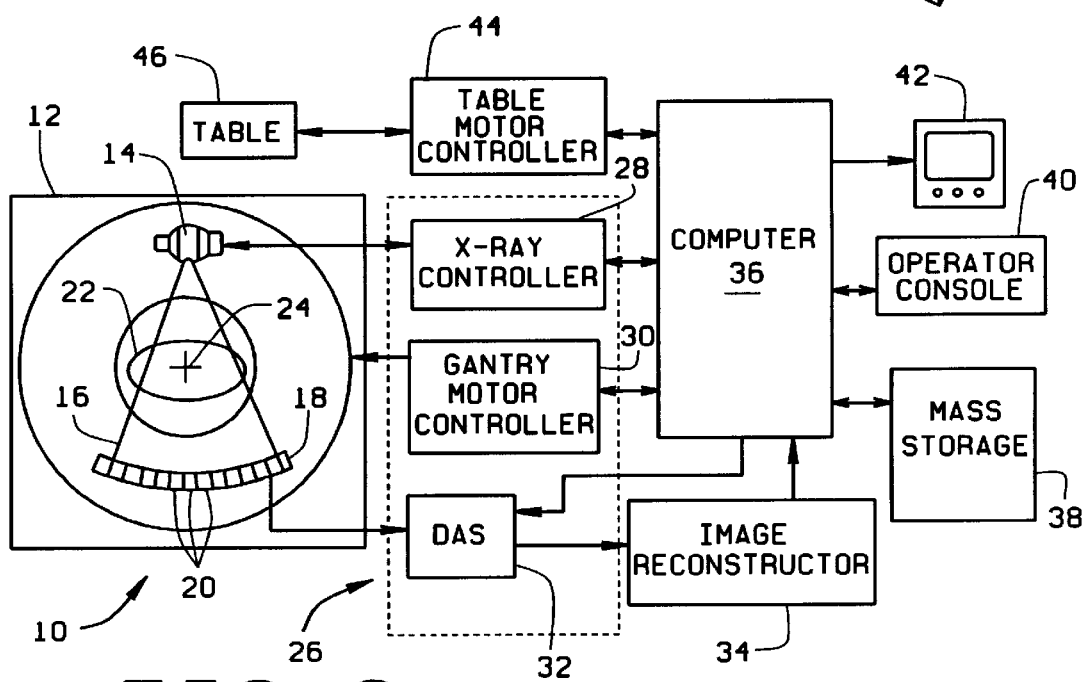
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor to the projection data in order to reconstruct an image. The weighting factor generally is based on both the fan angle and view angle.

Figure 3:
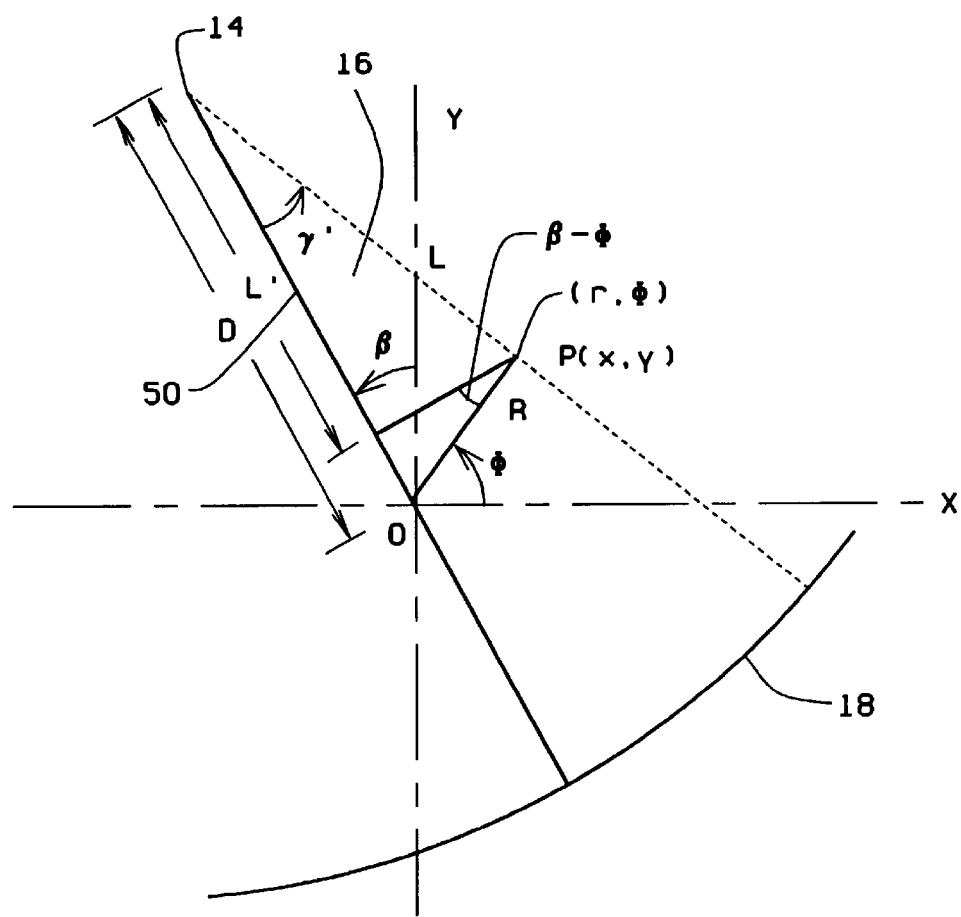
FIG. 3 is a schematic diagram of the geometry of the system illustrated in FIG. 1.

In one embodiment as shown in FIG. 3, which is a schematic diagram of the geometry of CT system 10, detector 18 is positioned substantially in the x-y plane P(x,y) of a Cartesian coordinate system having an origin O. X-ray source 14 projects x-ray beam 16, having an iso-center at origin O, toward detector 18 at a gantry angle β and a detector angle γ. For the purpose of the following discussion, D denotes a distance between x-ray source 14 and the iso-center of CT system 10. L denotes a distance between x-ray source 14 and a point of interest (r, φ), where r is a distance between origin O and point of interest (r, φ), and φ is an angle between the x-axis and the line connecting point of interest (r, φ) and origin O. A helical reconstruction algorithm f(r, φ) for reconstructing a 3D image corresponding to point of interest (r, φ) may be defined by the equation:

$$f(r,\phi) = \int_{\beta_0}^{\beta_0+\Pi} \frac{1}{L'^2} \int_{-\gamma_m}^{\gamma_m} p(\gamma',\beta)w(\gamma',\beta-\beta_0)g(\gamma-\gamma')D\cos^3\gamma' d\gamma' d\beta$$

where:
p(γ', β) is data, or projections, acquired at detector angle γ' and gantry angle β;
w(γ', β−β₀) is a helical weighting function;
Dcos³γ is a scaling factor;
g(γ) is a convolution reconstruction filter for the fan beam; and
L' is the projected distance on a central ray of the point of interest (r, φ) to the x-ray source.

For a HI algorithm, w(γ, β) is selected so that the projections are interpolated along the line β=π−2γ and is written as:

$$w(\gamma,\beta) = \begin{cases} \dfrac{\beta}{\pi-2\gamma}, & 0 \le \beta \le \pi-2\gamma \\ \dfrac{2\pi-\beta}{\pi+2\gamma}, & \pi-2\gamma < \beta < 2\pi. \end{cases}$$

As a result, the weighting function approaches zero at either end of the data set and near unity in the middle of the data set. The HE algorithm is different from the HI algorithm in that the weighting function is slightly negative on both ends of the data set and slightly larger than unity in the middle of the data set as written as:

$$w(\gamma,\beta) = \begin{cases} \dfrac{\beta+2\gamma}{\pi+2\gamma}, & 0 \le \beta \le \pi-2\gamma \\ \dfrac{2\pi-\beta-2\gamma}{\pi-2\gamma}, & \pi-2\gamma < \beta < 2\pi \end{cases}$$

Figure 4:
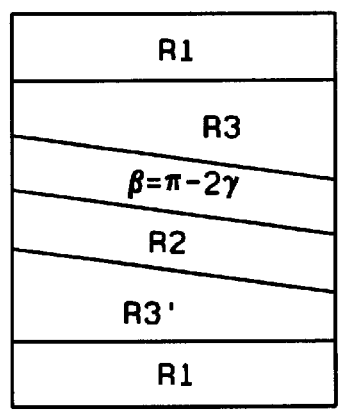
FIG. 4 is a radon space diagram of the projection data.

As a result of the weights for both the HI and HE algorithms being near zero at the start and end of a scan, R1 as shown in FIG. 4 depicting a Radon space representation of the helical sampling pattern, the start (R1) and end (R1) projection data contributes very little to the formation of the final image. Conversely, because of the redundant sampling pairs for R1 correspond to the projection data near the middle of the scan, region R2, the contribution from these samples makes a large contribution to the final image. If the size of the scanned object changes in the Z direction, the boundaries in the final image will correspond to R2 as a result of the R1 being negligible. In regions R3 and R3', however, the boundaries of the object are contributed nearly equally from R3 and R3'. Modeling the boundaries formed by the projections as ramp functions, a boundary estimate is determined. Applying equal weights to the R3' and R3, the estimated boundary is illustrated as combined boundary in FIG. 5. Note that the composite boundary is highly intensity dependent so that when the intensity is selected near the peak of the object intensity, the composite boundary is closer to that of R3'. If, however, the intensity is selected near the background intensity, the composite boundary is closer to R3. Therefore, utilizing the combined boundary to generate the 3D image results in periodical rings or grooves superimposed on the surface of the 3D object.

In accordance with one embodiment of the present invention, a 3D image generation algorithm reduces artifacts by determining the object boundaries using an optimal threshold intensity. More specifically, referring to FIG. 5, it can be observed that when the intensity is selected near a mid-point between the object intensity and the background intensity, the composite boundary is neither biased toward R3 nor R3', i.e., the composite boundary is roughly in the middle of R3 and R3'. In one embodiment, the intensity threshold level is selected to be in a range of 30% to 70% of the maximum intensity level to minimize the artifacts. For example, the intensity threshold level may be selected to be 50% between the maximum intensity level and the background intensity. By utilizing the 50% intensity threshold level, the boundary is consistent with the boundaries defined by R2 due to R2 being located half-way between R3' and R3. As a result, the 3D image artifacts are minimized.

In another embodiment where the threshold level is not alterable, or due to other restrictions the operator cannot alter the threshold level, an adaptive correction algorithm determines a boundary shift, or error, based on a starting angle of the scan, the rate of change of the object boundary, in Z, the helical weighting function, and the selection of the threshold. Utilizing the determined boundary shift, each boundary location may be adjusted by the boundary shift.

Specifically, after scanning the object and collecting the projection data, an estimated slope of the object boundary is determined by comparing the boundaries of neighboring slices. For example, using information representing the object surface, the angle formed by the surface of the object and the incident light angle are used to determine the shading of the object, using methods known in the art. After determining the estimated slope of the object boundary, a boundary error is determined. The boundary error is a function of the projection angle, the reconstruction algorithm, and the shape of the object. Specifically, for a given boundary location, the shape of the projection boundary, R3 and R3' shown in FIG. 4, are determined.

Utilizing the boundary location and the starting angle of the scan, unique weights are determined to apply to data from complementary sampling pairs R3 and R3'. For example and in one embodiment utilizing a helical extrapolative (HE) algorithm, the weights are defined by the equation:

$$w(\gamma, \beta) = \begin{cases} \dfrac{\beta + 2\gamma}{\pi + 2\gamma}, & 0 \le \beta \le \pi - 2\gamma \\ \dfrac{2\pi - \beta - 2\gamma}{\pi - 2\gamma}, & \pi - 2\gamma < \beta < 2\pi \end{cases}$$

In an alternative embodiment utilizing a helical interpolative (HI) algorithm, the weights are defined by the equation:

$$w(\gamma, \beta) = \begin{cases} \dfrac{\beta}{\pi - 2\gamma}, & 0 \le \beta \le \pi - 2\gamma \\ \dfrac{2\pi - \beta}{\pi + 2\gamma}, & \pi - 2\gamma < \beta < 2\pi \end{cases}$$

Figure 6:
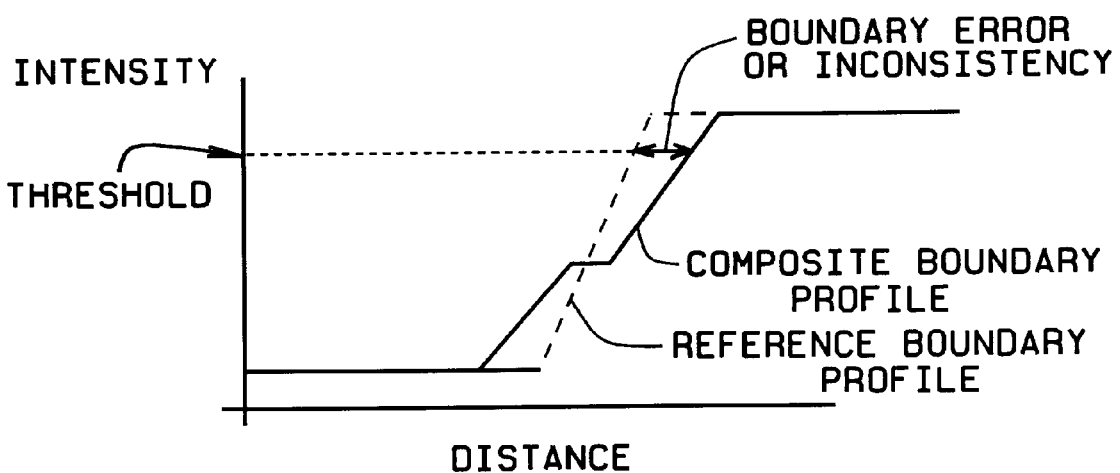
FIG. 6 is an intensity/distance function illustrating a boundary error in accordance with one embodiment of the present invention.
Figure 7:
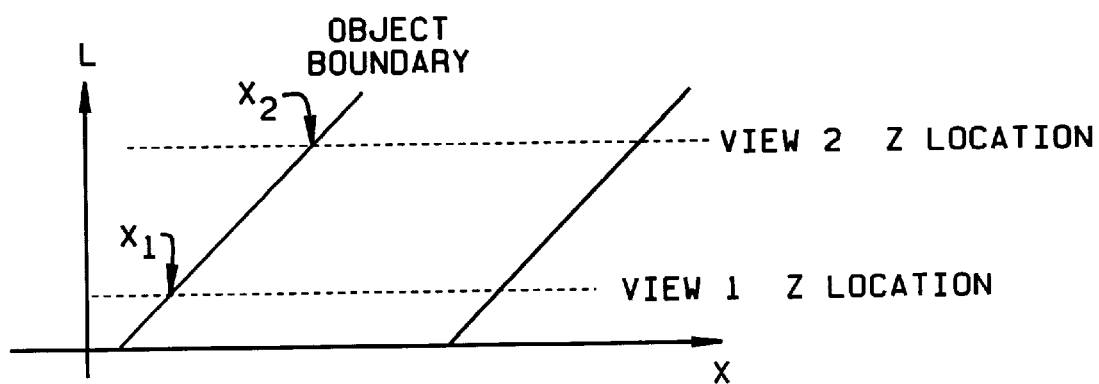
FIG. 7 is a schematic diagram of a helical composite boundary profile.
Figure 8:
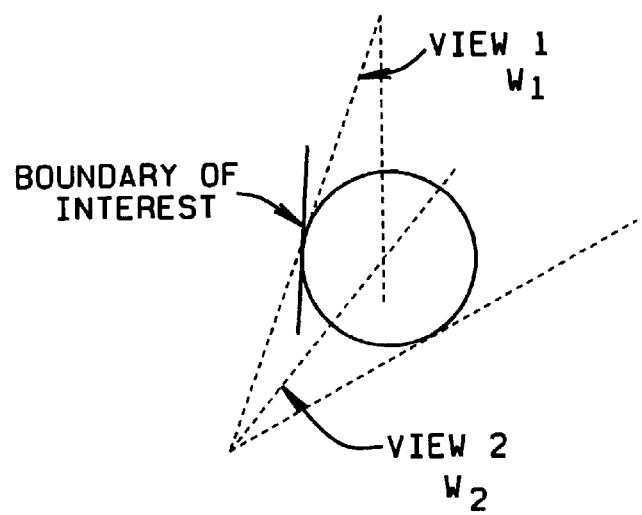
FIG. 8 is a schematic diagram of an axial composite boundary profile.

A composite boundary profile is then determined by applying the determined weights to the projection data. In one embodiment utilizing a helical scan, as illustrated in FIG. 6, the composite boundary may be written as:

$$g(x) = w_1 g_1(x - x_1) + w_2 g_2(x - x_2)$$

where:
  $g_1, g_2$ are object boundary profiles if an axial scan were taken;
  $w_1, w_2$ are helical reconstruction weights associated with views that are perpendicular to the boundary which form the complimentary sampling pairs;
  $x_1, x_2$ are object boundary locations at two views that are perpendicular to the boundary and form the complimentary sampling pair, as shown in FIGS. 7 and 8.

The object boundary profiles for $g_1, g_2$ for the axial scan can be determined by:

$$g(x) = \Gamma_{\frac{h}{k}} \otimes f$$

where:

$$\Gamma_{\frac{h}{k}}(x) = \begin{cases} 0 & x \le 0 \\ \dfrac{kx}{h} & 0 < x < \dfrac{h}{k} \\ 1 & \text{Other} \end{cases}$$

f is an edge response of an imaging system;
k is a slope of the object boundary in x-z plane;
h is a slice thickness;
x is an image index variable; and
$\otimes$ represents a convolution.

Figure 5:
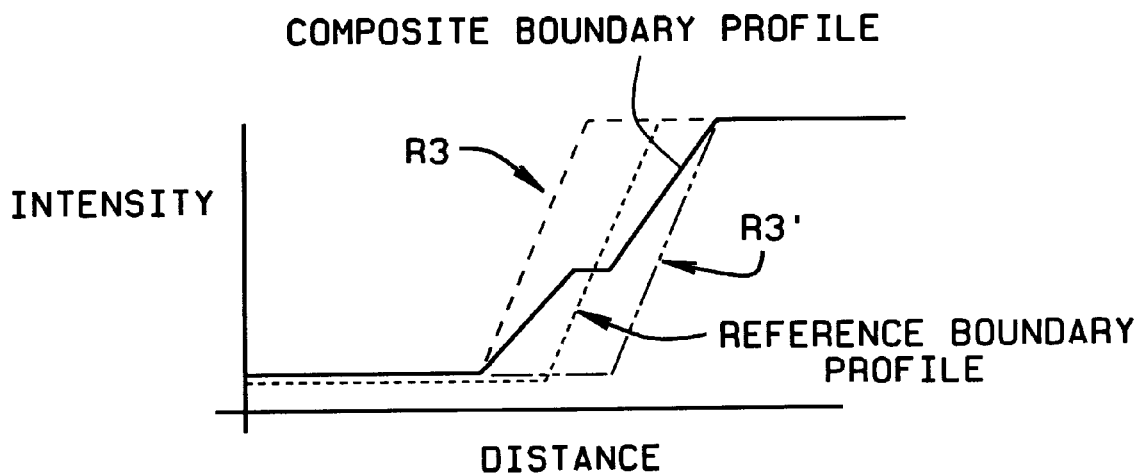
FIG. 5 is an intensity/distance function.

After determining the composite boundary profile, the profile shape is compared to a non-composite profile shape, as shown by the thick dotted line, referred to as a reference boundary profile, in FIG. 5. The reference profile is substantially the same as the composite profile boundary formed by regions R1 and R2. Therefore, the difference depicts the "inconsistency" of the composite boundaries between different regions. With the selected threshold for boundary determination, the difference between the composite boundary and the reference boundary can be easily determined, as shown in FIG. 6. Therefore, in one embodiment, the determined boundary from the composite boundary profile will be shifted, or adjusted, by an amount substantially equal to the determined boundary error. This shift is shown as "error" or "inconsistency" in FIG. 6. Note that the new boundary location will now be consistent with the boundaries formed by regions R1 and R2. Therefore, 3D image artifacts are reduced or removed.

In another embodiment, an adaptive filter is applied to the composite boundary profile to remove the boundary location dependency on the threshold selection. Specifically, in one embodiment, an adaptive filter is applied to the image data slices to smooth the object boundaries.

Referring to FIG. 6, the shapes of the composite boundary profile and the reference boundary profile are different. Due to the composite profile being uniquely determined based on the previous equations, a filter may be created to map the composite profile to the reference profile. As a result of the composite boundary profile changing with the helical weight, the start angle of the data set, and the slope of the object boundary in Z, in one embodiment, the filter is an adaptive filter. In one embodiment, based on FIG. 6, the filter is substantially a sharpening filter.

Alternatively, an arbitrary shape profile may be selected as the reference profile. For example, in one embodiment, one of the composite boundaries is selected and then the other profiles are forced to be substantially equal to the reference profile. As described above, an adaptive filter may be used. In addition, the adaptive filter may be a smoothing type or a sharpening type, depending on the relative shapes between the composite boundary profile and the reference boundary profile. In an alternative embodiment, the boundary locations are directly modified during the 3D model generation based on the determined boundary error.

In another alternative embodiment, the starting angles of each of the images are forced to be substantially equal. In one embodiment, non-overlapped reconstruction is performed. Specifically, images generated in this mode will be substantially not overlapped in the Z direction. In addition, the weights, i.e., $w_1$ and $w_2$, are forced to be substantially unchanged from slice to slice, to eliminate or reduce the 3D artifacts.

The above described algorithms facilitate reducing artifacts in 3D image reconstruction. Such algorithms also are not believed to significantly increase the processing time needed to generate such images.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. In addition, the composite profiles may be pre-stored or parameterized to reduce the computational cost, i.e., performed faster, of performing the above described methods. Accordingly, the spirit and scope of the invention are to be limited only by the terms of the appended claims.

What is claimed is:

1. An imaging system for reducing artifacts in a 3D image of an object, said system comprising an x-ray source and a detector away, said system configured to:
   scan the object;
   reconstruct an image of the object;
   select a threshold intensity level of the reconstructed image; and
   determine boundaries of the object using the reconstructed image and the selected threshold intensity.

2. A system in accordance with claim 1 wherein to scan the object, said system configured to collect a plurality of slices of object data.

3. A system in accordance with claim 2 wherein a starting angle for each of said plurality of slices of object data are substantially equal.

4. A method of reducing artifacts in an image of an object acquired in an imaging system, said method comprising the steps of:
   scanning the object;
   selecting a threshold intensity level;
   determining boundaries of the object;
   determining the slope of the object boundaries; and
   determining a boundary error.

5. A method in accordance with claim 4 wherein said method further comprises the step of adjusting the object boundaries.

6. A method in accordance with claim 5 wherein adjusting the boundaries comprises the step of adjusting the boundaries by an amount substantially equal to the determined boundary error.

7. A method in accordance with claim 4 further comprising the step of determining a composite boundary profile of the object.

8. A method in accordance with claim 7 wherein the composite boundary profile for an axial scan is:

$$g(x) = \Gamma_{\frac{h}{k}} \otimes f$$

where:

$$\Gamma_{\frac{h}{k}}(x) = \begin{cases} 0 & x \leq 0 \\ \frac{kx}{h} & 0 < x < \frac{h}{k} \\ 1 & \text{Other} \end{cases}$$

f is an edge response of an imaging system;
k is a slope of the object boundary in x-z plane;
h is a slice thickness;
x is an image index variable; and
$\otimes$ represents a convolution.

9. A method in accordance with claim 8 wherein the composite boundary profile for a helical scan is:

$$g(x) = w_1 g_1(x-x_1) + w_2 g_2(x-x_2)$$

where:
$g_1$, $g_2$ are object boundary profiles if an axial scan were taken;
$w_1$, $w_2$ are helical reconstruction weights associated with views that are perpendicular to the boundary which form a complimentary sampling pair;
$x_1$, $x_2$ are object boundary locations at two views that are perpendicular to the boundary and form the complimentary sampling pair.

10. A method in accordance with claim 7 further comprising the step of filtering the composite boundary profile.

11. A method in accordance with claim 10 wherein said filtering the composite boundary profile comprises the step of applying a smoothing filter.

12. A method in accordance with claim 10 wherein said filtering the composite boundary profile comprises the step of applying a sharpening filter.

13. A method of seducing artifacts in an image of an object acquired in an imaging system, said method comprising the steps of:

scanning the object with an imaging system;

reconstructing an image of the object;

selecting a threshold intensity level of the reconstructed image; and determining boundaries of the object using the reconstructed image and the selected threshold intensity.

14. A method in accordance with claim 1 wherein scanning the object comprises the step of collecting a plurality of slices of object data.

15. A method in accordance with claim 14 wherein a starting angle for each of the plurality of slices of object data are substantially equal.

16. A method in accordance with claim 1 further comprising the step of generating a three-dimensional image of the object.

17. A method of reducing artifacts in an image of an object acquired in an imaging system, said method comprising the steps of:

scanning the object;

selecting a threshold intensity level from a range between 30% and 70% of a maximum threshold intensity and background intensity; and determining boundaries of the object.

18. An imaging system for reducing artifacts in a 3D image of an object, said system comprising an x-ray source and a detector array, said system configured to:

scan the object;

reconstruct an image of the object;

select a threshold intensity level;

determine boundaries of the object;

determine a slope of said object boundaries; and determine a boundary error.

19. A system in accordance with claim 18 wherein said system further configured to adjust said object boundaries.

20. A system in accordance with claim 19 wherein to adjust said boundaries, said system configured to adjust said boundaries by an amount substantially equal to said determined boundary error.

21. A system in accordance with claim 18 further configured to determine a composite boundary profile of the object.

22. A system in accordance with claim 21 wherein said system is configured to perform an axial scan.

23. A system in accordance with claim 22 wherein said composite boundary profile is:

$$g(x) = \Gamma_{\frac{h}{k}} \otimes f$$

where:

$$\Gamma_{\frac{h}{k}}(x) = \begin{cases} 0 & x \leq 0 \\ \frac{kx}{h} & 0 < x < \frac{h}{k} \\ 1 & \text{Other} \end{cases}$$

f is an edge response of an imaging system;

k is a slope of the object boundary in x-z plane;

h is a slice thickness;

x is an image index variable; and $\otimes$ represents a convolution.

24. A system in accordance with claim 21 wherein said system is configured to perform a helical scan.

25. A system in accordance with claim 24 wherein said composite boundary profile is:

$$g(x) = w_1 g_1(x-x_1) + w_2 g_2(x-x_2)$$

where:

$g_1$, $g_2$ are object boundary profiles if an axial scan were taken;

$w_1$, $w_2$ are helical reconstruction weights associated with views that are perpendicular to the boundary which form a complimentary sampling pair;

$x_1$, $x_2$ are object boundary locations at two views that are perpendicular to the boundary and form the complimentary sampling pair.

26. A system in accordance with claim 18 further configured to filter said composite boundary profile.

27. A system in accordance with claim 26 wherein to filter said composite boundary profile, said system configured to apply a smoothing filter.

28. A system in accordance with claim 26 wherein to filter said composite boundary profile, said system configured to apply a sharpening filter.

* * * * *

UNITED STATES PATENT AND TRADEMARK OFFICE
CERTIFICATE OF CORRECTION

PATENT NO.       : 6,215,841 B1                                Page 1 of 1
APPLICATION NO.  : 09/162283
DATED            : April 10, 2001
INVENTOR(S)      : Jiang Hsieh It is certified that error appears in the above-identified patent and that said Letters Patent is hereby corrected as shown below:

Column 8, line 65, please delete "seducing" and substitute - - reducing - -.

Signed and Sealed this

Twenty-ninth Day of August, 2006

JON W. DUDAS
*Director of the United States Patent and Trademark Office*